US010188781B2

(12) United States Patent
Saito

(10) Patent No.: US 10,188,781 B2
(45) Date of Patent: Jan. 29, 2019

(54) METHOD OF MANUFACTURING HEAT EXCHANGER AND HEAT EXCHANGER

(71) Applicant: TERUMO KABUSHIKI KAISHA, Tokyo (JP)

(72) Inventor: Takashi Saito, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 195 days.

(21) Appl. No.: 15/221,732

(22) Filed: Jul. 28, 2016

(65) Prior Publication Data

US 2016/0331882 A1    Nov. 17, 2016

Related U.S. Application Data

(63) Continuation of application No. PCT/JP2015/050244, filed on Jan. 7, 2015.

(30) Foreign Application Priority Data

Jan. 31, 2014   (JP) ................. 2014-018076

(51) Int. Cl.
  *A61M 1/16* (2006.01)
  *F28D 21/00* (2006.01)
  (Continued)

(52) U.S. Cl.
  CPC ........ *A61M 1/1698* (2013.01); *A61M 1/1629* (2014.02); *B01D 63/02* (2013.01);
  (Continued)

(58) Field of Classification Search
  CPC .............. A61M 1/1698; A61M 1/1629; A61M 2207/00; B29C 53/8083; B29C 53/665;
  (Continued)

(56) References Cited

U.S. PATENT DOCUMENTS

| 5,261,981 A | 11/1993 | Schneider et al. |
| 2012/0277653 A1 | 11/2012 | Olsen et al. |

(Continued)

FOREIGN PATENT DOCUMENTS

| JP | H0568547 U | 9/1993 |
| JP | 2002369883 | 12/2002 |
| WO | 2015020197 A1 | 12/2015 |

OTHER PUBLICATIONS

European Patent Office, European Search Report, Reference No. MUB16-3403EP, Application No. 15742888.9-1602 / 3100751 PCT/JP2015050244, Applicant—Termuo Kabushiki Kaisha, dated Sep. 17, 2017.

*Primary Examiner* — John C Hong

(74) *Attorney, Agent, or Firm* — MacMillan, Sobanski & Todd, LLC

(57) ABSTRACT

A heat exchanger has a hollow fiber membrane layer comprised of a plurality of hollow fiber membrane conduits each of which has a hollow portion allowing a heat medium to pass therethrough. The conduits are derived by winding a base cord of the hollow fiber membrane onto a cylindrical body. The winding follows a generally helical trajectory around the longitudinal axis of the cylindrical body with a plurality of continuous round trips from the first end to the second end and turning back at each respective end, wherein each round trip completes a number of circumferential revolutions N, wherein N is greater than or equal to one, and wherein N is less than two.

9 Claims, 13 Drawing Sheets

(51) Int. Cl.
    *B01D 63/02*       (2006.01)
    *B29C 53/66*       (2006.01)
    *B29C 53/80*       (2006.01)
    *B29L 31/00*       (2006.01)
    *B29L 31/18*       (2006.01)

(52) U.S. Cl.
    CPC ........ *B29C 53/665* (2013.01); *B29C 53/8083* (2013.01); *F28D 21/0015* (2013.01); *A61M 2207/00* (2013.01); *B01D 2313/22* (2013.01); *B01D 2313/90* (2013.01); *B29L 2031/18* (2013.01); *B29L 2031/753* (2013.01); *F28D 2021/005* (2013.01)

(58) Field of Classification Search
    CPC ................ B01D 63/02; B01D 2313/90; B01D 2313/22; F28D 21/0015; F28D 2021/005; B29L 2031/753; B29L 2031/18
    See application file for complete search history.

(56) References Cited

U.S. PATENT DOCUMENTS

2015/0010433 A1    1/2015    Takeuchi et al.
2015/0010434 A1    1/2015    Takeuchi et al.

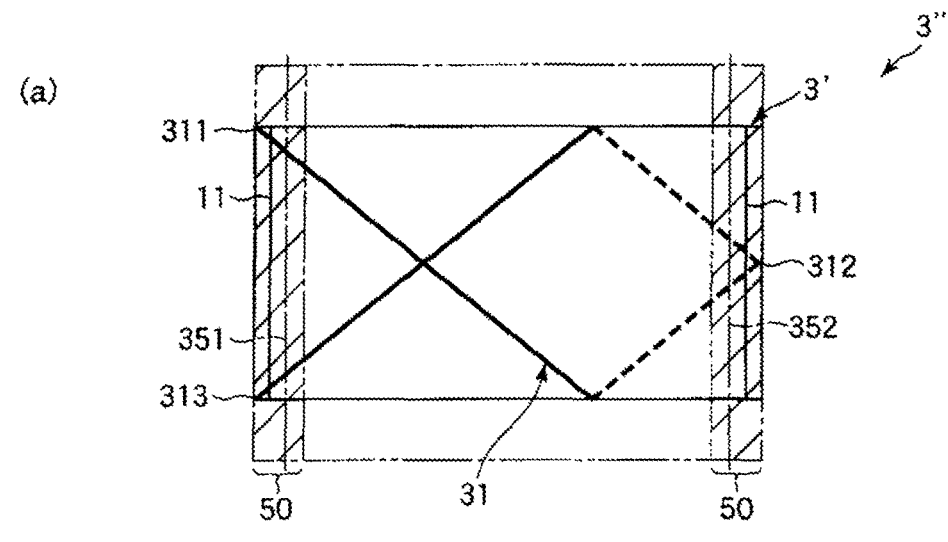
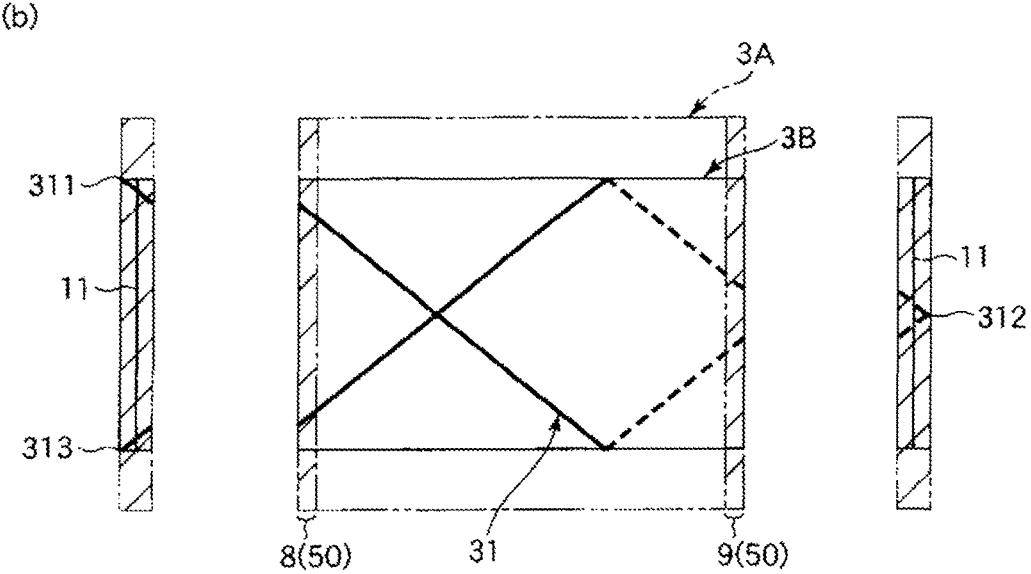
FIG.10

METHOD OF MANUFACTURING HEAT EXCHANGER AND HEAT EXCHANGER

CROSS REFERENCE TO RELATED APPLICATIONS

This application is a continuation of PCT Application No. PCT/JP2015/050244, filed Jan. 7, 2015, based on and claiming priority to Japanese application no. 2014-018076, filed Jan. 31, 2014, both of which are incorporated herein by reference in their entirety.

TECHNICAL FIELD

The present invention relates to a method of manufacturing a heat exchanger and a heat exchanger apparatus.

BACKGROUND ART

In the related art, there is a known heat exchanger having a hollow fiber membrane layer which is configured to include a plurality of hollow fiber membranes so as to form an overall shape of a cylindrical body. A hollow fiber sheet disclosed in PTL 1 can be applied to the hollow fiber membrane layer forming the cylindrical body shape. In the hollow fiber sheet disclosed in Japanese Registered Utility Model No. 2579299, the plurality of hollow fiber membranes are disposed in substantially parallel to each other so as to be the woof, and the woof is woven together with the warp, thereby forming a bamboo blind-shaped sheet. Such a bamboo blind-shaped hollow fiber sheet can serve as the hollow fiber membrane layer by being caused to have a cylindrical body shape. In this case, each of the hollow fiber membranes of the hollow fiber sheet is disposed substantially parallel to the central axis of the cylindrical body.

In the heat exchanger including the hollow fiber membrane layer having such a configuration, when the heat medium passes through the inside of the hollow fiber membrane, the passing distance thereof for obtaining sufficient heat exchange is not ensured. Therefore, in order to improve the heat exchanger effectiveness, there is a need to increase the number of times of winding each of the hollow fiber membranes by winding the hollow fiber membrane about the central axis of the cylindrical body. However, as the number of times of winding the hollow fiber membrane increases, the overall length of the hollow fiber membrane becomes elongated. In proportion thereto, there is a problem of an increase of a pressure loss of the heat medium passing through the inside of the hollow fiber membrane. Accordingly, there is a concern that the heat exchanger effectiveness deteriorates.

In addition, in a case where a heat exchanger using a bamboo blind-shaped hollow fiber sheet is applied to an oxygenator for use in cardiac support, gaps among and between the hollow fiber membranes can be configured to allow blood to pass through.

However, as the number of times of winding each of the hollow fiber membranes increases, the total volume of the gaps among and between the hollow fiber membrane increases. As a result thereof, the quantity of blood passing through the gaps, that is, a blood filling amount (i.e., blood volume contained within the oxygenator) also increases, and thus, the burden to a patient becomes significant.

SUMMARY OF INVENTION

Technical Problem

An object of the present invention is to provide a method of manufacturing a heat exchanger that is excellent in heat exchanger effectiveness and is able to reduce a filling amount of a fluid when the fluid which becomes a target subjected to heat exchange thereof passes through between hollow fiber membranes, and the heat exchanger that is manufactured by the manufacturing method.

Solution to Problem

The aforementioned object is achieved by the present invention which provides a method of manufacturing a heat exchanger including a hollow fiber membrane layer that is configured to include a plurality of hollow fiber membranes each of which has a hollow portion allowing a heat medium to pass therethrough and is obtained from a base material in which the plurality of hollow fiber membranes are accumulated so as to form an overall shape of a cylindrical body. The manufacturing method includes a winding step of winding each of the hollow fiber membranes about an axis of the cylindrical body while the hollow fiber membrane is caused to be wound along an axial direction of the cylindrical body so as to obtain the base material. In the winding step, each of the hollow fiber membranes is wound about the axis of the cylindrical body within a range from one round to less than two rounds during one round trip in which the hollow fiber membrane starts from one side toward the other side of the cylindrical body in the axial direction, turns back at the other side, and returns to the one side again.

The hollow fiber membrane may preferably be wound so as to satisfy the following Expression 1:

Traverse [mm/rot]×$N$=traverse oscillation width×2± (outer diameter of hollow fiber membrane+gap between hollow fiber membranes adjacent to each other)×total number of hollow fiber membranes(where $N$ satisfies 1≤$N$<2).

Preferably, N satisfies 1.2≤N≤1.6. In addition, the round trip is preferably repeated multiple times.

In the winding step, a turned-back portion may be preferably fixed when each of the hollow fiber membranes turns back at the other side. A fixing method may preferably be utilized in which the turned-back portion is pressed by a flexible string-like body or a flexible belt-like body, in which the turned-back portion is subjected to heat-melting, or in which an adhesive is used.

The method of manufacturing a heat exchanger may further including a cutting step of cutting both end portions of the base material so as to obtain the hollow fiber membrane layer. Both the end portions of the base material include the turned-back portion which is fixed through the winding step. In the cutting step, the turned-back portion is removed from the base material. The method of manufacturing a heat exchanger may preferably employ a hollow fiber membrane made from a polyolefin-based resin. Furthermore, an outer diameter of the hollow fiber membrane is preferably equal to or less than 1 mm.

In another aspect of the invention, a method is provided for manufacturing a heat exchanger comprised of a plurality of hollow fiber membrane conduits each of which has a hollow portion allowing a heat medium to pass therethrough. The method comprises providing a cylindrical body for supporting the fiber membrane layer, wherein the cylindrical body has an outer surface defining a longitudinal axis and first and second longitudinal ends. A continuous base cord of hollow fiber membrane is wound onto the cylindrical body along a generally helical trajectory around the longitudinal axis with a plurality of continuous round trips from the first end to the second end and turning back at each respective end. Each round trip completes a number of circumferential revolutions N, wherein N is greater than or equal to one, and wherein N is less than two. Longitudinal end portions are cut from the wound fiber membrane layer, thereby removing turning-back portions to introduce open ends for the hollow fiber membrane conduits.

Advantageous Effect of Invention

According to the present invention, the overall length of each of the hollow fiber membranes for one round trip can be shortened as much as possible. Accordingly, in the hollow fiber membrane layer, a pressure loss of the heat medium passing through the hollow portion of each of the hollow fiber membranes is reduced. Accordingly, the hollow fiber membrane layer becomes excellent in the heat exchanger effectiveness.

In addition, the diameter of the hollow fiber membrane can be decreased in size as much as possible by the quantity of the reduced pressure loss of the heat medium, that is, it is possible to realize reduction of the hollow fiber membrane in size. Accordingly, the volume of the hollow fiber membrane layer can be decreased. Therefore, it is possible to reduce a filling amount of a fluid which becomes a target subjected to heat exchange.

BRIEF DESCRIPTION OF DRAWINGS

FIG. 10 is a view sequentially illustrating a step of cutting the base material illustrated in FIG. 8.

DESCRIPTION OF EMBODIMENTS

Hereinafter, a method of manufacturing a heat exchanger and the heat exchanger according to the present invention will be described in detail based on preferable embodiments illustrated in the accompanying drawings.

First Embodiment

Note that, in FIGS. 1, 3, 4, and 7 to 10 (similar in FIGS. 11 and 16), the left side will be referred to as "left" or "left-hand side (one side)", and the right side will be referred to as "right" or "right-hand side (the other side)". In addition, in FIGS. 1 to 6 (similar in FIGS. 11 and 16), the inner side of the oxygenator will be described as "blood inlet side" or "upstream side", and the outer side thereof will be described as "blood outlet side" or "downstream side".

An oxygenator 10 illustrated in FIGS. 1 to 5 has an overall shape which is substantially columnar. The oxygenator 10 is equipped with a heat exchanger including a heat exchange section 10B which is provided on the inner side thereof and performs heat exchange with respect to blood, and an oxygenator section 10A as a gas exchange section which is provided on an outer circumferential side of the heat exchange section 10B and performs gas exchange with respect to blood. For example, the oxygenator 10 is used while being installed in an extracorporeal blood circulation circuit.

The oxygenator 10 has a housing 2A. The oxygenator section 10A and the heat exchange section 10B are stored inside the housing 2A.

The housing 2A is configured to include a cylindrical housing main body 21A, a dish-shaped first cap 22A which seals a left end opening of the cylindrical housing main body 21A, and a dish-shaped second cap 23A which seals a right end opening of the cylindrical housing main body 21A.

The cylindrical housing main body 21A, the first cap 22A, and the second cap 23A are configured to be made from resin materials. The first cap 22A and the second cap 23A are fixedly attached to the cylindrical housing main body 21A through a method such as fusion or bonding performed by using an adhesive.

A tubular blood outlet port 28 is formed in an outer circumferential portion of the cylindrical housing main body 21A. The blood outlet port 28 protrudes toward a substantially tangential direction on an outer circumferential surface of the cylindrical housing main body 21A (see FIG. 5).

A tubular gas outlet port 27 is formed in the first cap 22A in a protruding manner. In addition, a blood inlet port 201 protrudes from an end surface of the first cap 22A such that the central axis thereof becomes eccentric with respect to the center of the first cap 22A.

Figure 1:
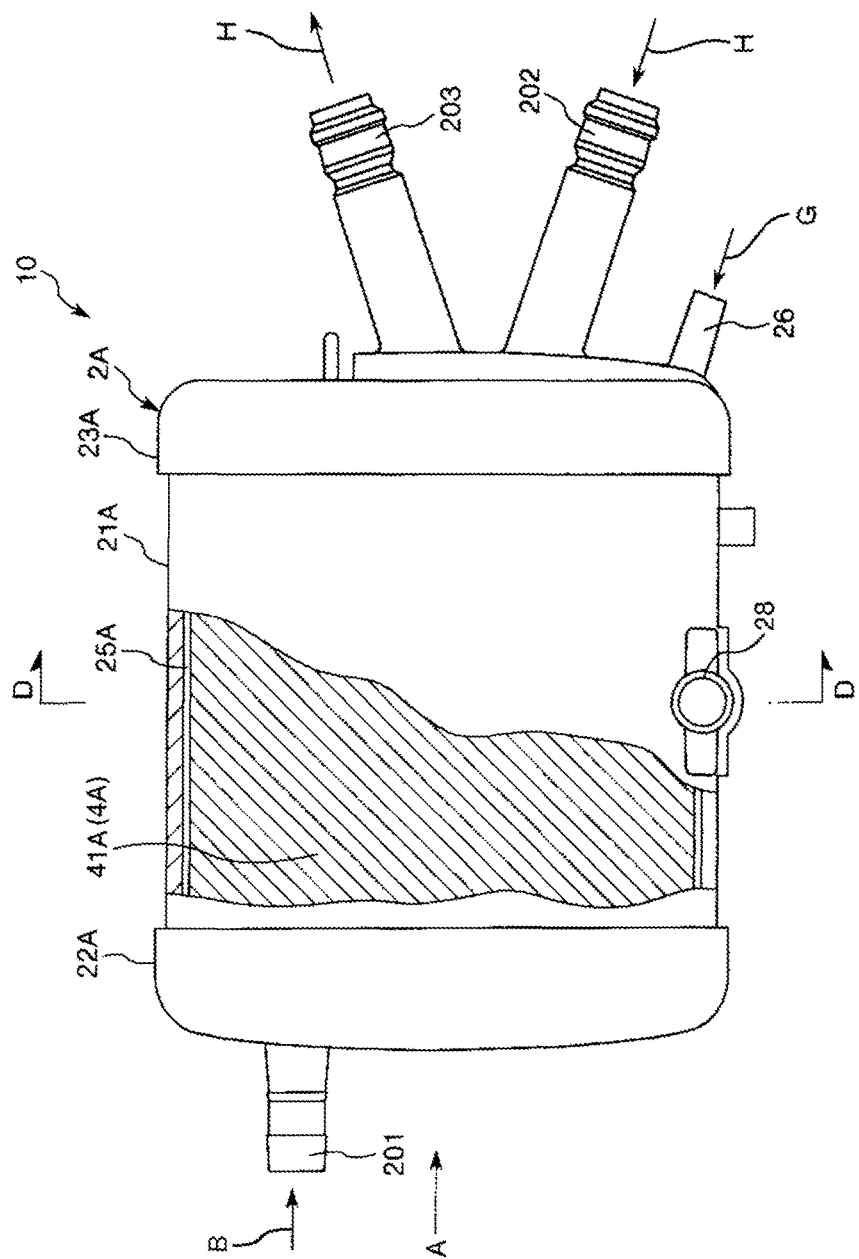
FIG. 1 is a plan view of an oxygenator in which a heat exchanger manufactured through a method of manufacturing a heat exchanger of the present invention (first embodiment) is applied.
Figure 2:
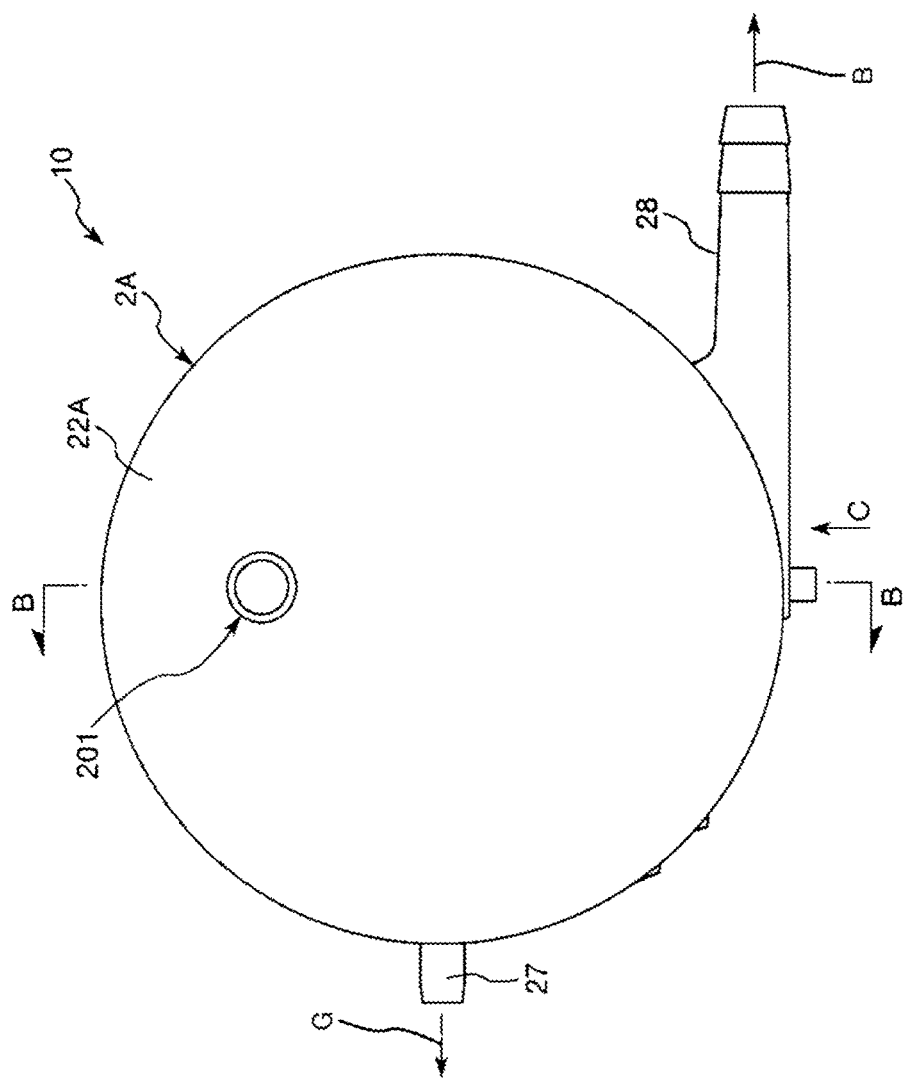
FIG. 2 is a side view of the oxygenator which is illustrated in FIG. 1 and viewed in an arrow A direction.

The gas outlet port 27 is formed in the outer circumferential portion of the first cap 22A such that the central axis thereof intersects the center of the first cap 22A (see FIG. 2).

A tubular gas inlet port 26, a heat medium inlet port 202, and a heat medium outlet port 203 are formed in the second cap 23A in protruding manners. The gas inlet port 26 is formed at an edge portion on the end surface of the second cap 23A. The heat medium inlet port 202 and the heat medium outlet port 203 are respectively formed at a substantially central portion on the end surface of the second cap 23A. In addition, each of the centerlines of the heat medium inlet port 202 and the heat medium outlet port 203 slightly inclines with respect to the centerline of the second cap 23A.

Note that, in the present invention, the overall shape of the housing 2A does not need to be completely columnar. For example, the housing 2A may have a partially deleted (e.g., flattened) shape or a shape to which a different portion is added.

Figure 3:
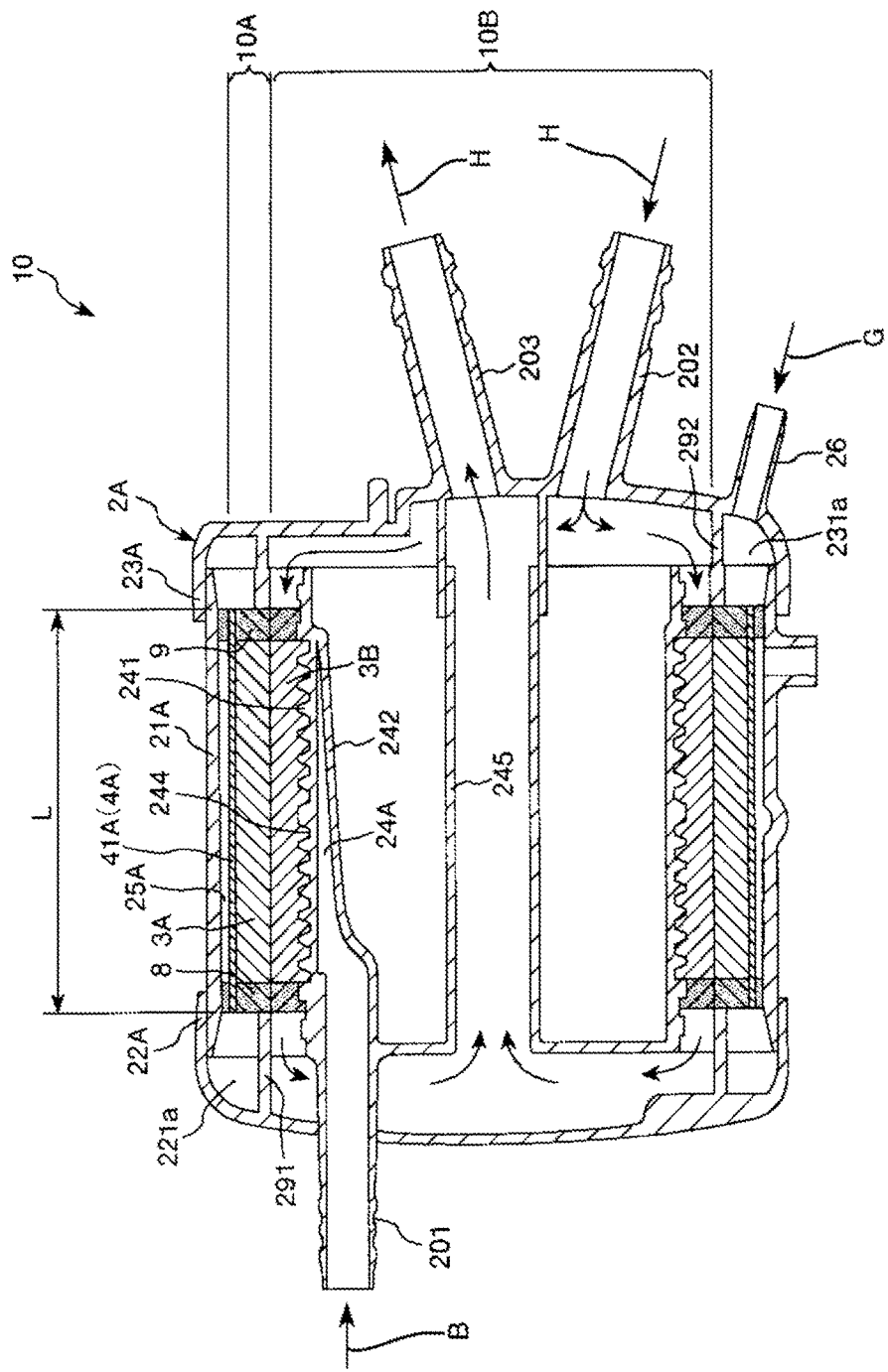
FIG. 3 is a cross-sectional view taken along line B-B in FIG. 2.
Figure 4:
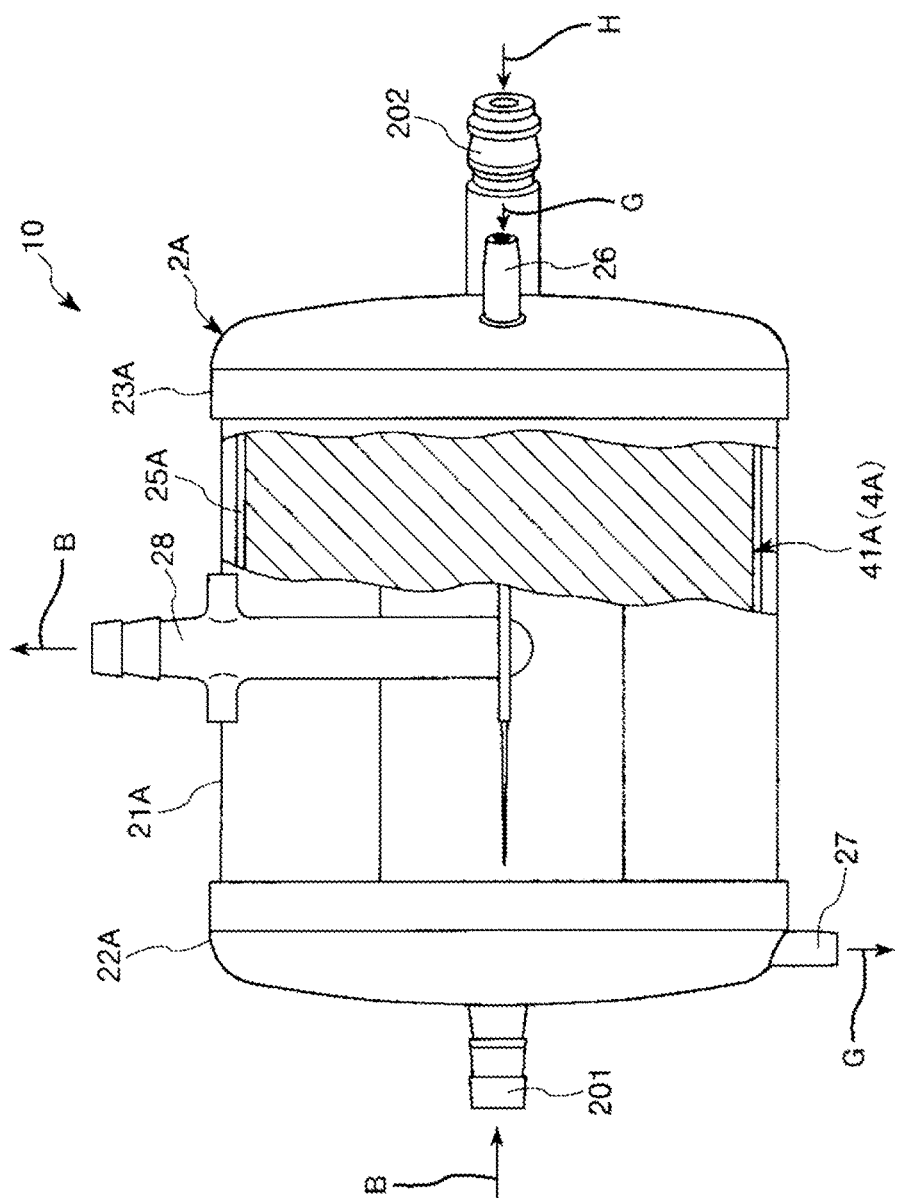
FIG. 4 is a side view which is viewed in an arrow C direction in FIG. 2.
Figure 5:
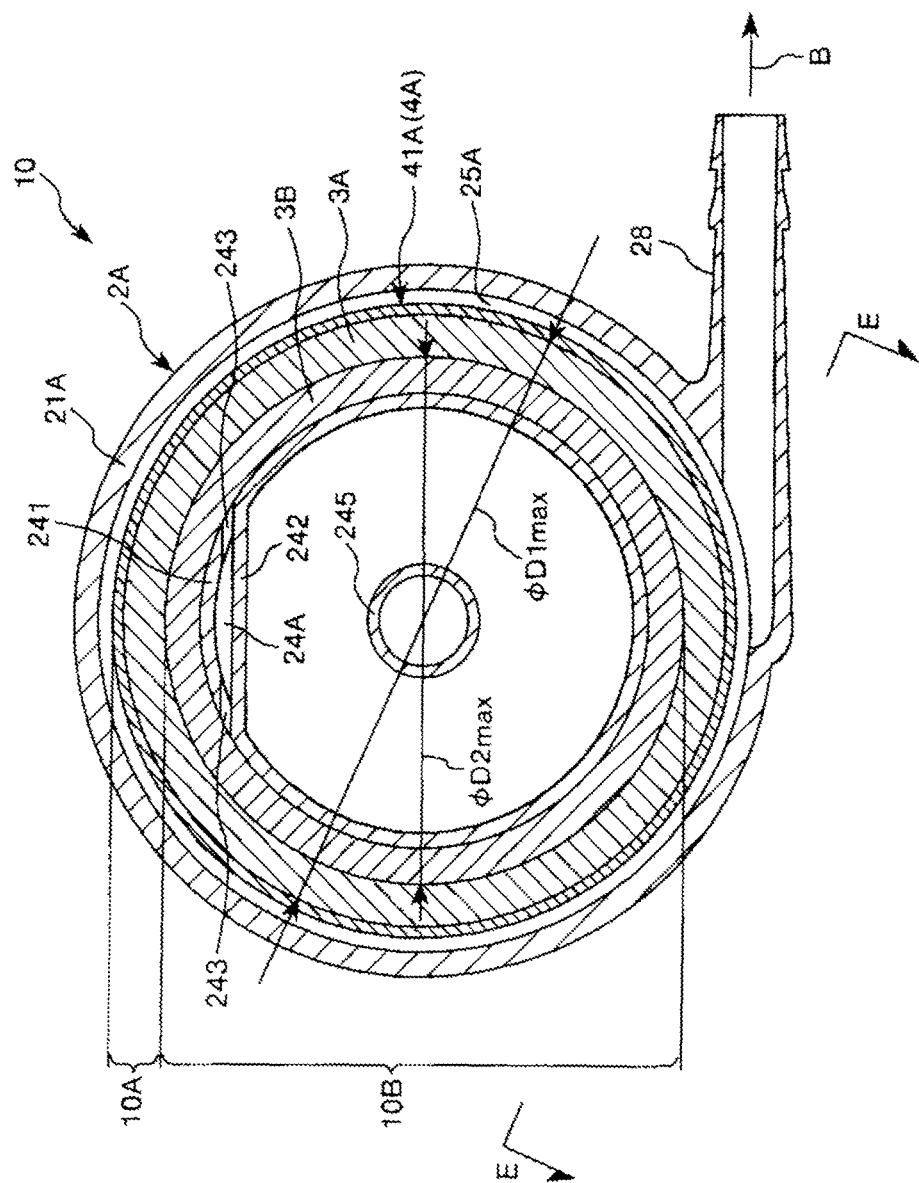
FIG. 5 is a cross-sectional view taken along line D-D in FIG. 1.

As illustrated in FIGS. 3 and 5, the oxygenator section 10A formed to have a cylindrical shape along an inner circumferential surface thereof is stored inside the housing 2A. The oxygenator section 10A is configured to include a cylindrical hollow fiber membrane layer 3A and a filter member 41A as air bubble removing means 4A which is provided on the outer circumferential side of the hollow fiber membrane layer 3A. The hollow fiber membrane layer 3A and the filter member 41A are disposed in order of first the hollow fiber membrane layer 3A and then the filter member 41A according to a flow direction from the blood inlet side.

In addition, the heat exchange section 10B formed to have a cylindrical shape along the inner circumferential surface thereof is installed on the inner side of the oxygenator section 10A. The heat exchange section 10B has a hollow fiber membrane layer 3B.

Figure 6:
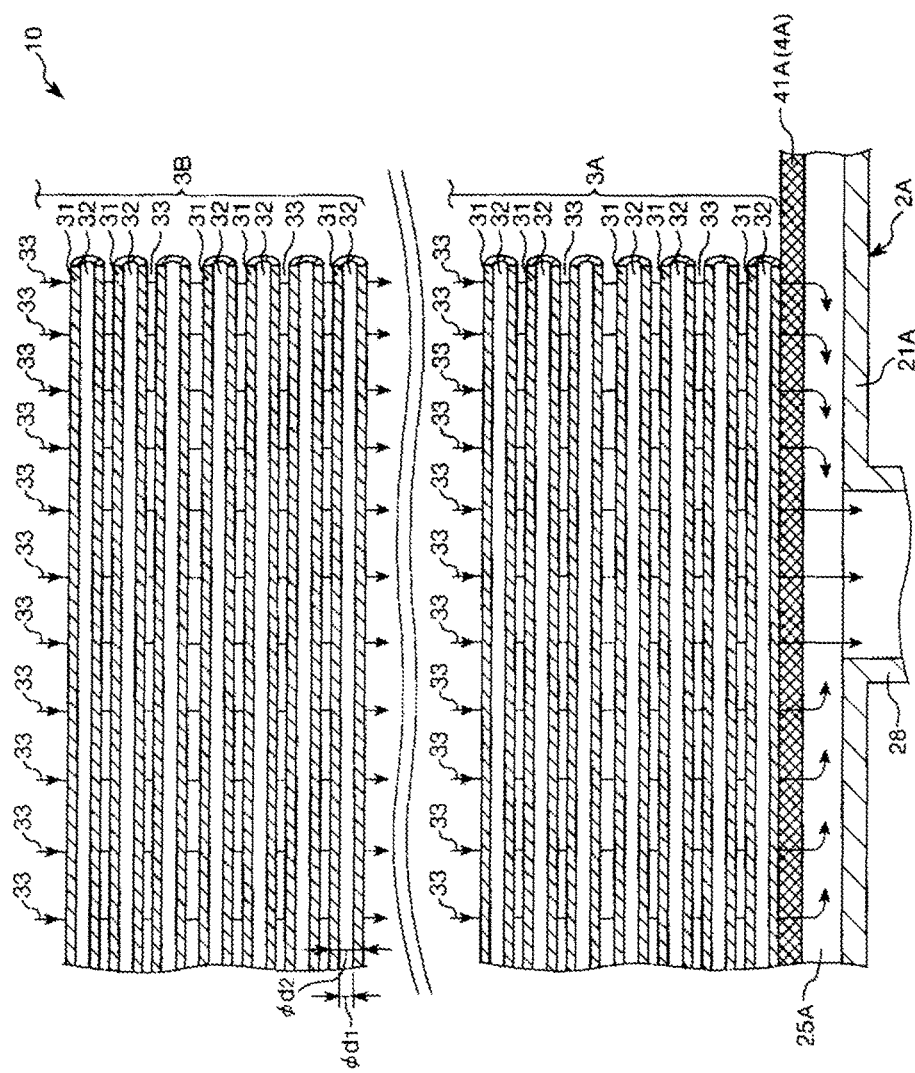
FIG. 6 is a cross-sectional view taken along line E-E in FIG. 5.

As illustrated in FIG. 6, each of the hollow fiber membrane layers 3A and 3B is configured to include a plurality of tubular hollow fiber membranes 31. The hollow fiber membranes 31 are accumulated in a layered state, thereby forming laminated layers. The number of the lamination layers is not particularly limited. However, for example, 3 layers to 40 layers are preferable. Note that, each of the hollow fiber membranes 31 in the hollow fiber membrane layer 3A has a function of gas exchange. Meanwhile, each of the hollow fiber membranes 31 in the hollow fiber membrane layer 3B has a function to perform heat exchange.

As illustrated in FIG. 3, both end portions of each of the hollow fiber membrane layers 3A and 3B are collectively fixed to the inner surface of the cylindrical housing main body 21A respectively by partitions 8 and 9. For example, the partitions 8 and 9 are configured to be made from potting materials such as polyurethane, silicone rubber, and the like; adhesives; or the like, wherein the tubular hollow membranes 31 extend through partitions 8 and 9. Moreover, an inner circumferential portion of the hollow fiber membrane layer 3B engages with an uneven portion 244 formed in an outer circumferential portion of a first cylinder member 241. Due to the engagement thereof and the fixed state formed by the partitions 8 and 9, the hollow fiber membrane layer 3B is reliably fixed to the cylindrical housing main body 21A. Accordingly, it is possible to reliably prevent positional misalignment of the hollow fiber membrane layer 3B from occurring while the oxygenator 10 is in use. In addition, the uneven portion 244 also functions as a flow path for circulating blood B throughout the hollow fiber membrane layer 3B in its entirety.

Note that, as illustrated in FIG. 5, the maximum outer diameter $\phi D1_{max}$ of the hollow fiber membrane layer 3A preferably ranges from 20 mm to 200 mm, and more preferably ranges from 40 mm to 150 mm. The maximum outer diameter $\phi D2_{max}$ of the hollow fiber membrane layer 3B preferably ranges from 10 mm to 150 mm, and more preferably ranges from 20 mm to 100 mm. In addition, as illustrated in FIG. 3, lengths L of the hollow fiber membrane layers 3A and 3B along the central axis direction preferably range from 30 mm to 250 mm, and more preferably range from 50 mm to 200 mm. According to such conditions, the hollow fiber membrane layer 3A becomes excellent in the function of gas exchange, and the hollow fiber membrane layer 3B becomes excellent in the function of heat exchange.

A blood flow path 33 through which the blood B flows from the upper side toward the lower side in FIG. 6 is formed on the outer side of the hollow fiber membranes 31 between the partition 8 and the partition 9 inside the housing 2A, that is, in gaps among the hollow fiber membranes 31.

A blood inlet side space 24A communicating with the blood inlet port 201 as a blood inlet portion for the blood B which has flowed in through the blood inlet port 201 is formed on the upstream side of the blood flow path 33 (see FIGS. 3 and 5).

The blood inlet side space 24A is a space defined by the cylindrical first cylinder member 241 and a plate piece 242 which is disposed on the inner side of the first cylinder member 241 and is disposed while facing a portion of the inner circumferential portion thereof. The blood B which has flowed into the blood inlet side space 24A can flow down throughout the blood flow path 33 in its entirety via a plurality of side holes 243 formed in the first cylinder member 241.

In addition, a second cylinder member 245 disposed so as to be concentric with the first cylinder member 241 is disposed on the inner side of the first cylinder member 241. As illustrated in FIG. 3, a heat medium H such as water, for example, which has flowed in through the heat medium inlet port 202 sequentially passes through a flow path (hollow portion) 32 of each of the hollow fiber membranes 31 in the hollow fiber membrane layer 3B on the outer circumferential side of the first cylinder member 241, and the inner side of the second cylinder member 245, thereby being discharged through the heat medium outlet port 203. In addition, when the heat medium H passes through the flow path 32 of each of the hollow fiber membranes 31, heat exchange (heating or cooling) is performed with respect to the blood B in contact with the hollow fiber membranes 31 along the blood flow path 33.

The filter member 41A having a function of capturing air bubbles present in the blood B flowing through the blood flow path 33 is disposed on the downstream side of the blood flow path 33.

The filter member 41A is configured as a substantially rectangular sheet-like member (hereinafter, will also be simply referred to as "sheet") and is formed by winding the sheet along the outer circumference of the hollow fiber membrane layer 3A. Both end portions of the filter member 41A are also fixedly attached by the partitions 8 and 9. Accordingly, the filter member 41A is fixed to the housing 2A (see FIG. 3). Note that, it is preferable that the filter member 41A is provided while causing the inner circumferential surface thereof to come into contact with the outer circumferential surface of the hollow fiber membrane layer 3A and to cover the substantially overall surface of the outer circumferential surface.

In addition, even though air bubbles are present in blood flowing through the blood flow path 33, the filter member 41A can capture the air bubbles (see FIG. 6). In addition, air bubbles captured by the filter member 41A are pressed due to the blood flow, thereby entering the inside of each of the hollow fiber membranes 31 in the vicinity of the filter member 41A. As a result thereof, the air bubbles are removed from the blood flow path 33.

In addition, a cylindrical gap is formed between the outer circumferential surface of the filter member 41A and the inner circumferential surface of the cylindrical housing main body 21A, and the gap forms a blood outlet side space 25A. A blood outlet portion is configured to include the blood outlet side space 25A and the blood outlet port 28 which communicates with the blood outlet side space 25A. In the blood outlet portion, due to the blood outlet side space 25A, it is possible to ensure a space in which the blood B permeating through the filter member 41A flows toward the blood outlet port 28, and thus, the blood B can be smoothly discharged.

As illustrated in FIG. 3, an annular rib 291 is formed on the inner side of the first cap 22A in a protruding manner. A first chamber 221a is defined by the first cap 22A, the rib 291, and the partition 8. The first chamber 221a is a gas outlet chamber from which gas G flows out. The left end opening of each of the hollow fiber membranes 31 in the hollow fiber membrane layer 3A is open to and communicates with the first chamber 221a. In the oxygenator 10, a gas outlet portion is configured to include the gas outlet port 27 and the first chamber 221a. Meanwhile, an annular rib 292 is also formed on the inner side of the second cap 23A in a protruding manner. A second chamber 231a is defined by the second cap 23A, the rib 292, and the partition 9. The second chamber 231a is a gas inlet chamber into which the gas G flows. The right end opening of each of the hollow fiber membranes 31 in the hollow fiber membrane layer 3A is open to and communicates with the second chamber 231a. In the oxygenator 10, a gas inlet portion is configured to include the gas inlet port 26 and the second chamber 231a.

Here, a flow of blood in the oxygenator 10 according to the present embodiment will be described. In the oxygenator 10, the blood B which has flowed in through the blood inlet port 201 sequentially passes through the blood inlet side space 24A and the side holes 243, thereby flowing into the heat exchange section 10B. In the heat exchange section 10B, the blood B flows through the blood flow path 33 toward the downstream direction and comes into contact with the outer surface of each of the hollow fiber membranes 31 of the heat exchange section 10B, thereby performing heat exchange (heating or cooling). The blood B which has been subjected to heat exchange as described above flows into the oxygenator section 10A.

In the oxygenator section 10A, the blood B flows further through the blood flow path 33 toward the downstream direction. Meanwhile, gas (oxygen-containing gas) supplied from the gas inlet port 26 is distributed from the second chamber 231a to the flow path 32 of each of the hollow fiber membranes 31 of the oxygenator section 10A and flows through the flow path 32. Thereafter, the gas is accumulated in the first chamber 221a and is discharged through the gas outlet port 27. The blood B flowing through the blood flow path 33 comes into contact with the outer surface of each of the hollow fiber membranes 31 of the oxygenator section 10A, there performing gas exchange, that is, addition of oxygen and decarbonation with respect to the gas G flowing through the flow path 32.

In a case where air bubbles are mixed in the blood B which has been subjected to gas exchange, the air bubbles are captured by the filter member 41A, thereby being prevented from flowing out to the downstream side of the filter member 41A.

As described above, the blood B which has been sequentially subjected to heat exchange and gas exchange and from which air bubbles have been removed flows out through the blood outlet port 28.

As described above, both the hollow fiber membrane layers 3A and 3B are configured to include the plurality of hollow fiber membranes 31. The hollow fiber membrane layer 3A and the hollow fiber membrane layer 3B have the same hollow fiber membranes 31 except that the purposes thereof are different from each other. Therefore, hereinafter, the hollow fiber membrane layer 3B will be representatively described.

An inner diameter $\phi d_1$ of each hollow fiber membrane 31 preferably ranges from 50 μm to 700 μm, and more preferably ranges from 70 μm to 600 μm (see FIG. 6). An outer diameter $\phi d_2$ of each hollow fiber membrane 31 preferably ranges from 100 μm to 1 mm, and more preferably ranges from 120 μm to 800 μm (see FIG. 6). Moreover, the ratio d1/d2 of the inner diameter $\phi d_1$ and the outer diameter $\phi d_2$ preferably ranges from 0.5 to 0.9, and more preferably ranges from 0.6 to 0.8. In each of the hollow fiber membranes 31 having such conditions, while the mechanical strength is retained, it is possible that an undesirable pressure loss due to flow resistance may occur when the heat medium H flows through the flow path 32 from one end of each individual hollow fiber membrane 31 to the other end. In addition thereto, the conditions contribute to maintaining the winding state of the hollow fiber membrane 31. For example, when the inner diameter $\phi d_1$ is greater than the upper limit value, the thickness of the hollow fiber membrane 31 becomes thin, and thus, the strength deteriorates depending on other conditions. In addition, when the inner diameter $\phi d_1$ is smaller than the lower limit value, a pressure loss when the heat medium H flows through the hollow fiber membrane 31 increases depending on other conditions.

In addition, a distance between the hollow fiber membranes 31 adjacent to each other in the wound layer more preferably ranges from 1/10 to 1/1 of $\phi d_2$.

A method of manufacturing a hollow fiber membrane 31 is not particularly limited. However, for example, a method of using extrusion molding can be employed. According to the method thereof, it is possible to manufacture the hollow fiber membrane 31 having predetermined inner diameter $\phi d_1$ and outer diameter $\phi d_{12}$. Note that, as the method of manufacturing a hollow fiber membrane 31 configured to form the hollow fiber membrane layer 3A, a method using drawing or solid-liquid phase separation can be employed.

As a configuration material for each of the hollow fiber membranes 31, for example, a hydrophobic polymer material such as polypropylene, polyethylene, polysulfone, polyacrylonitrile, polytetrafluoroethylene, and polymethylpentene, and the like is used. As the material thereof, a polyolefin-based resin is preferable, and polypropylene is more preferable. Selecting such resin materials contributes to maintaining the winding state of the hollow fiber membrane 31 and also contributes to reduction of the cost during the manufacture.

The hollow fiber membrane layer 3B can be obtained from a base material 3' in which the hollow fiber membrane 31 is wound so as to form the overall shape of a cylindrical body. The base material 3' is manufactured during the process of manufacturing in the manufacturing method of the present invention.

The present manufacturing method is a method of manufacturing the oxygenator 10 and includes a first step, a second step, a third step, a fourth step, a fifth step, and a sixth step. Subsequently, the method will be described.

Figure 8:
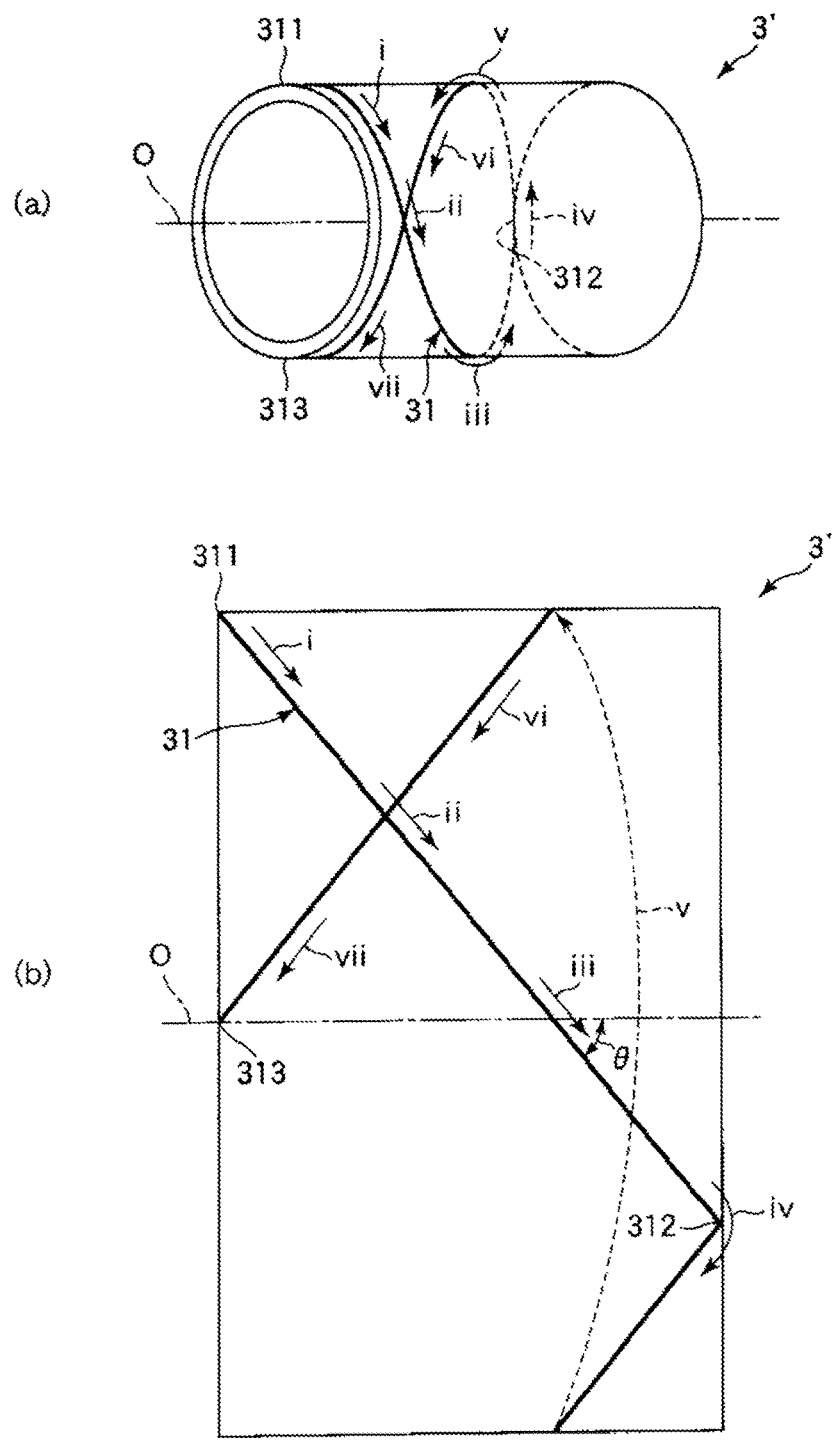
FIG. 8 is a view illustrating a base material obtained by the manufacturing apparatus illustrated in FIG. 7 (FIG. 8(a) is a perspective view and FIG. 8(b) is a development view).

As illustrated in FIG. 8, the first step is a winding step of winding the plurality of hollow fiber membranes 31 so as to form the overall shape of a cylindrical body, thereby obtaining the base material (primary base material) 3'. Note that, in FIG. 8 (also similar in FIG. 10), a winding path of one hollow fiber membrane 31 is representatively depicted.

Figure 7:
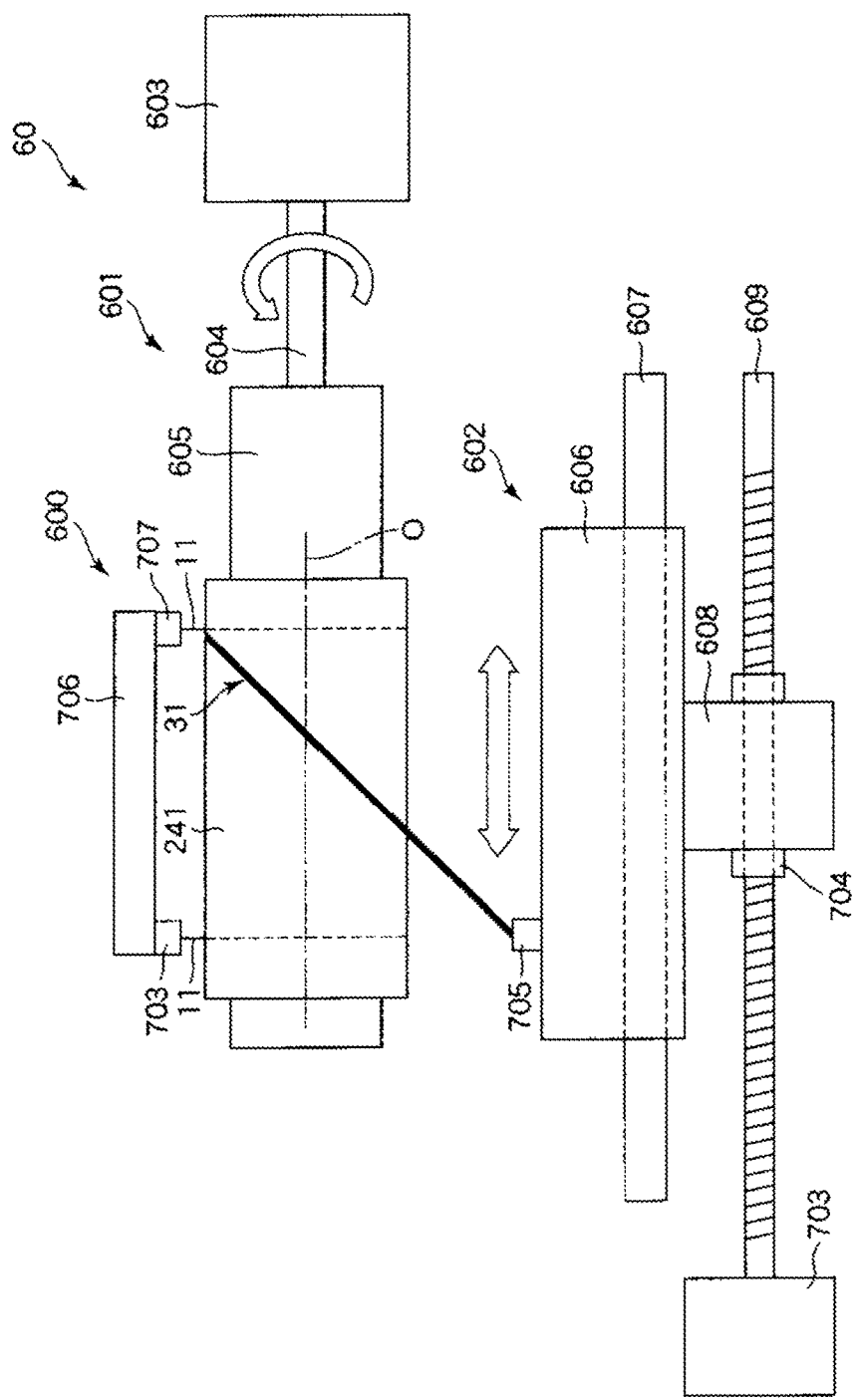
FIG. 7 is a view illustrating an apparatus used in the method of manufacturing a heat exchanger of the present invention.

In the first step, a winding apparatus 60 illustrated in FIG. 7 is used. The winding apparatus 60 includes tubular core rotation means 601, a winder 602, and a fixing device 600.

The tubular core rotation means 601 includes a motor 603, a motor shaft 604, and a core attachment member 605 fixed to the motor shaft 604. The first cylinder member 241 which is a portion of the housing 2A of the oxygenator 10 is attached to the core attachment member 605 and is rotated by the motor 603.

The winder 602 includes a main body portion 606 provided with a storage portion internally storing the hollow fiber membrane 31, and an ejection portion 705 which ejects the hollow fiber membrane 31 and moves in the axial direction (left-right direction in FIG. 7) of the main body portion 606. Moreover, the main body portion 606 is fixed to a linear table 608 moving on a linear rail 607, and a ball nut member 704. When a ball screw shaft 609 rotates in response to the driving of a motor 703, the ball nut member 704 can move in a direction parallel to the axial direction of the main body portion 606. The motor 703 can rotate normally and reversely and of which the driving is adjusted by a controller (not illustrated).

The fixing device 600 includes a main body portion 706 provided with a storage portion storing a fixing string (string-like body) 11 which fixes the hollow fiber membrane 31 wound around the first cylinder member 241, and an ejection portion 707 ejecting the fixing string 11 toward both of the end portions of the first cylinder member 241. When the hollow fiber membrane 31 is fixed by using the fixing string 11, the fixing string 11 ejected from the ejection portion 707 is wound around the hollow fiber membrane 31 on the first cylinder member 241 which is rotating, thereby being fixed. After being fixed, the fixing string 11 used for the fixing is cut from the fixing device 600 by a cutter (not illustrated).

In addition, the fixing string 11 is flexible, and for example, is configured to be made from a thermoplastic resin such as polyamide (example: nylon 6, nylon 46, nylon 66, nylon 610, nylon 612, nylon 11, nylon 12, nylon 6-12, and nylon 6-66) and the like, or a metal material such as stainless steel and the like. Accordingly, the hollow fiber membrane 31 can be fixed due to tensile force suitable for the fixing.

The first step is carried out by using the winding apparatus 60 having the above-described configuration. In the description below, one hollow fiber membrane 31 will be representatively described.

As illustrated in FIGS. 7 and 8, in the first step, the hollow fiber membrane 31 is wound about a central axis O while the hollow fiber membrane 31 is caused to be wound along the central axis O direction of the first cylinder member 241 (cylindrical body). In this case, the hollow fiber membrane 31 starts to be wound from a starting point 311 on the left side toward the right side in the central axis O direction. On the right side, the hollow fiber membrane 31 turns back at a turning-back point 312. Thereafter, the hollow fiber membrane 31 returns to the left side again, thereby reaching an ending point 313. In this manner, the hollow fiber membrane 31 is wound in order of the arrows i→ii→iii→iv→v→vi→vii in FIG. 8. During one round trip thereof, as illustrated in FIG. 8, the hollow fiber membrane 31 is wound as many as a predetermined number N of rounds. In the present embodiment, N is 1.5, and the hollow fiber membrane 31 is wound 1.5 rounds about the central axis O during one round trip. The above-described state will be referred to as "0.75 windings".

In the present invention, the range of the number N of rounds ranges from one round to less than two rounds, preferably ranges from more than one round to less than two rounds, and more preferably ranges from 1.2 rounds to 1.6 rounds. Accordingly, the number N of rounds is preferably a real number having a decimal within a range from more than 1 to less than 2. Note that, the range of the number N of rounds ranging "from one round to less than two rounds" refers to the number of circumferential revolutions as the hollow fiber membrane 31 is wound from a first end of first cylinder member 241 to a second end and then back to the first end. This is equivalently expressed by using the unit "winding", which refers to the number of circumferential revolutions occurring of a single conduit from one end to the other of cylinder member 241, and which preferably ranges from 0.5 windings to less than 1 winding.

In addition, as illustrated in FIG. 8(b), the hollow fiber membrane 31 inclines with respect to the central axis O. For example, an inclination angle (traverse angle) θ thereof preferably ranges from 40° to 70°, and more preferably ranges from 45° to 64°. When the inclination angle is less than 40°, the hollow fiber membrane 31 is required to be more firmly fixed to the end portion of the base material 3'. Thus, there is a possibility that it is difficult to manufacture the base material 3'. In addition, when the inclination angle exceeds 70°, the overall length of the hollow fiber membrane 31 (i.e., the helical or spiral length from one longitudinal end of cylindrical layer 3B to the other longitudinal end of each individual conduit) becomes excessively long, and a pressure loss of the heat medium H increases.

In addition, the inclination angle (traverse angle) θ changes in proportion to an increase of the number of windings. The rate of change between the traverse angles at the start and the end of winding becomes significant depending on the dimensions of the outer diameter of the cylindrical member to be wound or the necessary number of windings (heat transfer area). The above-described conditions also lead to the unevenness of the overall length of the hollow fiber in one heat exchanger. Therefore, in order to stabilize the performance, it is desirable to control the traverse angle by varying the traverse width in the winder, appropriately varying the number of windings, or the like. The rate of change in the present Example described below is approximately 8%, and it has been confirmed that such a rate does not affect the performance of heat exchange. Note that, the overall length of the base cord of hollow fiber membrane 31 to be wound in the present invention may be equal to approximately 2,000 m. However, the overall length is not limited thereto. The overall length varies depending on the conditions or the circumstances such as the outer diameter and the like of the hollow fiber membrane 31.

Figure 11:
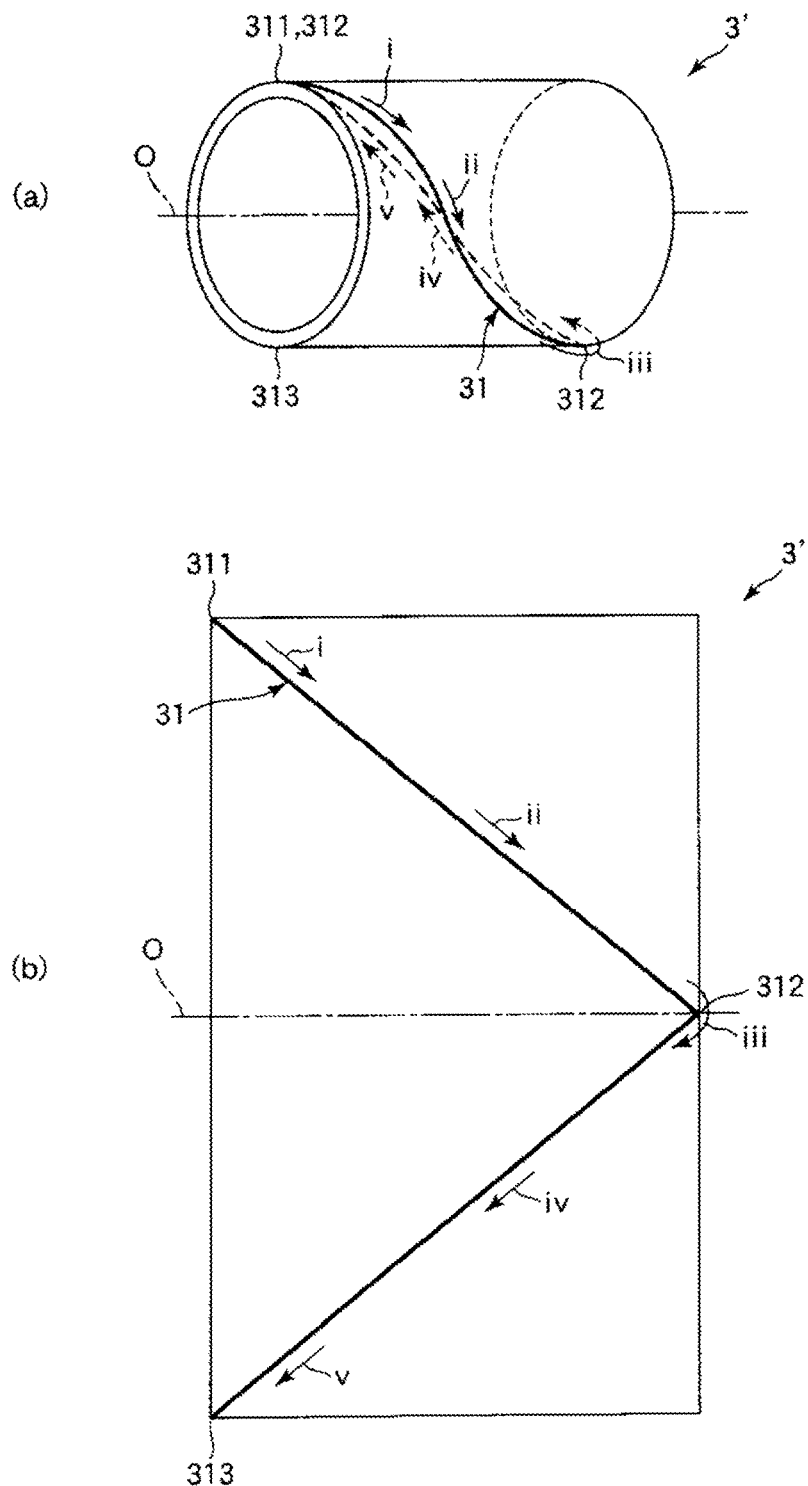
FIG. 11 is a view illustrating another configuration of the base material obtained by the method of manufacturing a heat exchanger of the present invention (FIG. 11(a) is a perspective view and FIG. 11(b) is a development view).

Alternatively, the base material 3' may have the configuration illustrated in FIG. 11, for example, in place of the configuration illustrated in FIG. 8. In the base material 3' illustrated in FIG. 11, the hollow fiber membrane 31 is wound in order of the arrows i→ii→iii→iv→v in FIG. 11. During one round trip thereof, the hollow fiber membrane 31 is wound one round about the central axis O, that is, "0.5 windings".

Figure 16:
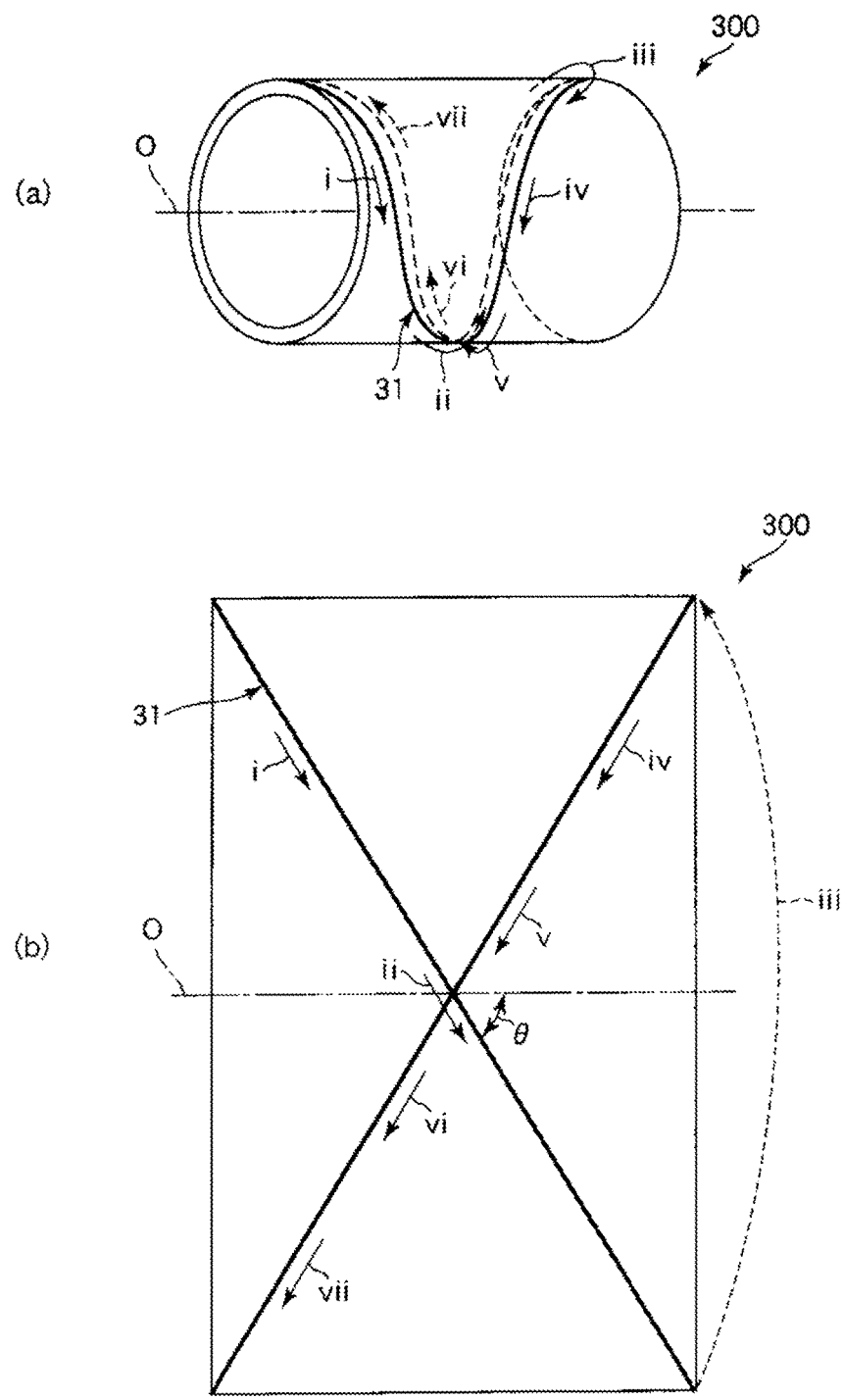
FIG. 16 is a view illustrating a base material configured to have the hollow fiber membrane which is wound in a winding state in the related art (FIG. 16(a) is a perspective view and FIG. 16(b) is a development view).

Incidentally, for example, there is an oxygenator in the related art having the hollow fiber membrane layer which is obtained from a base material 300 illustrated in FIG. 16. In the base material 300, the hollow fiber membrane 31 is wound in order of the arrows i→ii→iii→iv→v→vi→vii in FIG. 16, and is wound two rounds about the central axis O during one round trip. It is referred to as "1 winding". In this case, the number N of rounds of the hollow fiber membrane 31 is greater than that in the case of FIG. 8. In other words, the number N of rounds thereof deviates from the above-described range of the number N of rounds, and the overall length of the hollow fiber membrane 31 per one round trip becomes long. As a result thereof, a pressure loss of the heat medium H passing though the inside of the hollow fiber membrane 31 increases, and thus, the heat exchanger effectiveness in the hollow fiber membrane layer deteriorates. In addition, an increase of the pressure loss of the heat medium H also leads to a need to increase the diameter of the hollow fiber membrane 31. Furthermore, the volume of the hollow fiber membrane layer increases as well. In this case, a blood filling amount increases, thereby being a burden to a patient.

However, as described above, in the present invention, the hollow fiber membrane 31 is wound 1.5 rounds about the central axis O during one round trip. The overall length of the hollow fiber membrane 31 becomes short by the quantity of the difference with respect to that in the related art. Accordingly, in the hollow fiber membrane layer 3B, a pressure loss of the heat medium H passing through the inside of the hollow fiber membrane 31 is reduced. Accordingly, the hollow fiber membrane layer 3B becomes excellent in the heat exchanger effectiveness. In addition, the volume of the gap between the hollow fiber membranes 31 adjacent to each other can also be reduced by the quantity of the reduced overall length of the hollow fiber membrane 31, and the filling amount of the blood B passing through the gap which is the blood flow path 33 can also be reduced.

In addition, in the hollow fiber membrane layer 3B, when the hollow fiber membrane 31 is wound as described above, the arrangement density of the hollow fiber membranes 31 can be set high as much as possible, and the outer diameter $\phi d_2$ of the hollow fiber membrane 31 can be set small as much as possible within the above-described range. Due to the high arrangement density, the number of the hollow fiber membranes 31 increases. Accordingly, the heat exchanger effectiveness is improved. In addition, due to reduction in size, the blood B passing transversely through the inside of the hollow fiber membrane layer 3B can be split into many branches. Accordingly, a chance for the blood B to come into contact with the hollow fiber membrane 31 increases. Due to the above-described reason, the heat exchanger effectiveness is also improved. Moreover, due to reduction in size, it is possible to realize miniaturization of the oxygenator 10.

In addition, due to the simple manufacturing method in which the hollow fiber membrane 31 is wound, it is possible to easily and reliably obtain the hollow fiber membrane layer 3B.

In addition, as described above, the hollow fiber membrane 31 can be continuously molded through extrusion molding. The above-described method is suitable for mass production, and the manufacturing cost can also be suppressed.

As described above, the hollow fiber membrane 31 makes one round trip via the starting point 311, the turning-back point 312, and the ending point 313. The round trip is repeated multiple times. Accordingly, the hollow fiber membrane 31 can be continuously supplied to the first cylinder member 241. Therefore, the hollow fiber membrane layer 3B can be promptly manufactured, the manufacturing time can be shortened, and the cost can be suppressed. Moreover, the winding apparatus 60 operates so as to satisfy the following Expression (1):

Traverse [mm/rot]×N=traverse oscillation width×2± (outer diameter of hollow fiber membrane+gap between hollow fiber membranes adjacent to each other)×total number of hollow fiber membranes(where N satisfies 1≤N<2).

Here, the term "traverse" denotes the moving amount of the hollow fiber membrane 31 when the first cylinder member 241 makes one rotation about the central axis O. The term "traverse oscillation width" denotes the moving amount of the ejection portion 705.

When Expression (1) is satisfied, the hollow fiber membranes 31 can be disposed in line while the gaps thereamong are controlled, and the hollow fiber membrane layer 3B can be preferably formed (see FIG. 9(b)).

Figure 9:
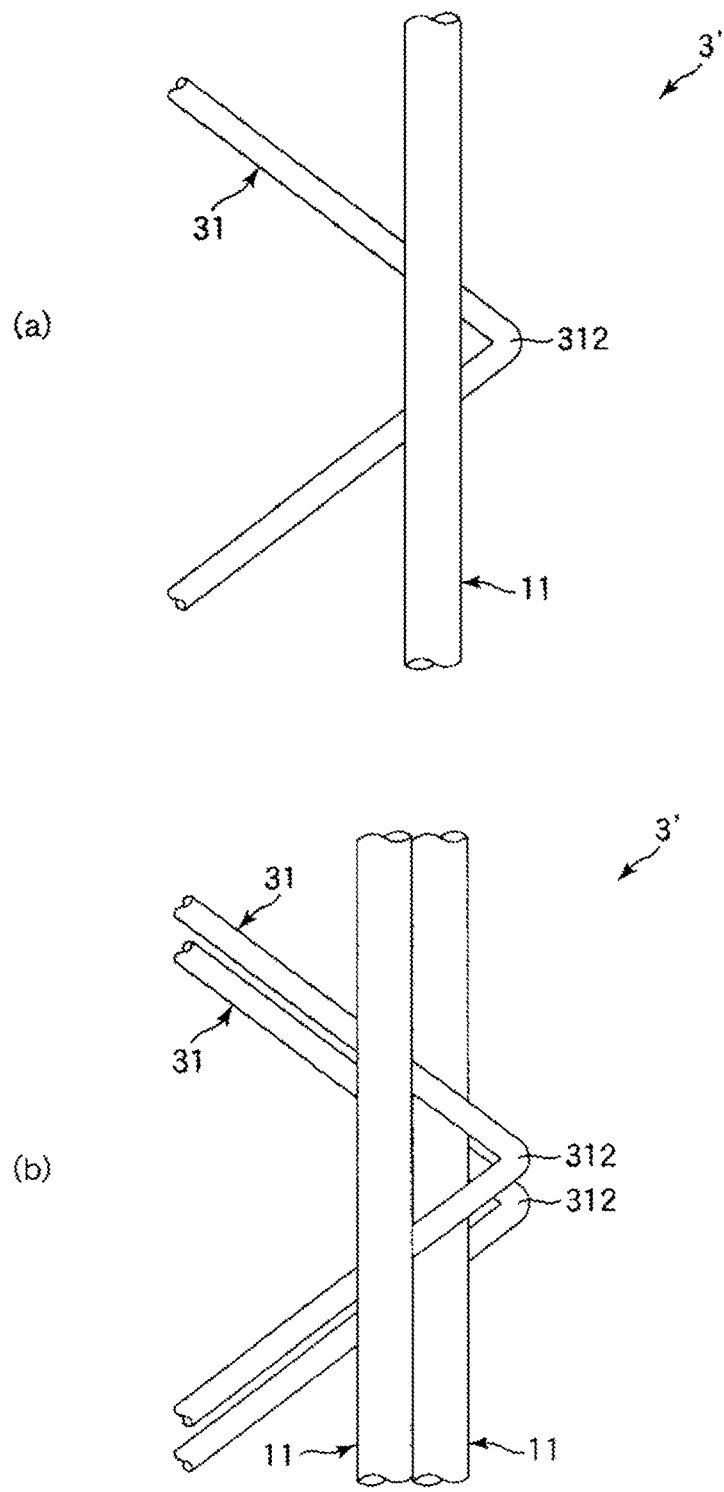
FIG. 9 is a view illustrating a fixed state of a hollow fiber membrane in the base material illustrated in FIG. 8.

As illustrated in FIG. 9, in the hollow fiber membrane 31, a portion in the vicinity of the turning-back point 312 (turned-back portion) is fixed when turning back at the turning-back point 312. The fixing is performed by pressing the turned-back portion with the fixing string 11 supplied from the fixing device 600 of the winding apparatus 60. Accordingly, the hollow fiber membrane 31 reliably turns back at the turning-back point 312. Therefore, the hollow fiber membrane 31 can reliably make a round trip, and thus, the state is maintained. Note that, as described below, the fixing string 11 remains with no change in the base material 3' but is removed when forming the final hollow fiber membrane layer 3B.

In addition, in the hollow fiber sheet disclosed in Japanese Registered Utility Model No. 2579299, the warp has been required to bunch the hollow fiber membranes. The warp causes induction of thrombus or the like. However, in the present invention, the winding state of the hollow fiber membrane 31 is maintained due to the fixing string 11. Accordingly, the warp can be omitted. Therefore, it is possible to prevent thrombus or the like from occurring.

The second step is a winding step in which the hollow fiber membrane 31 that becomes the hollow fiber membrane layer 3A is wound further onto the base material 3'. Accordingly, it is possible to obtain a secondary base material 3" illustrated in FIG. 10(a).

In the second step, the winding apparatus 60 is used with no change, and the hollow fiber membrane 31 is wound in a winding state similar to that in the first step.

After the second step is completed, the secondary base material 3" in the first cylinder member 241 is detached from the winding apparatus 60 in its entirety.

The third step is a storing step in which the filter member 41A is wound around and fixed to the secondary base material 3" and the secondary base material 3" is stored in the cylindrical housing main body 21A together with the first cylinder member 241.

The fourth step is a fixing step in which the secondary base material 3" is fixed to the cylindrical housing main body 21A. When the secondary base material 3" is fixed, a potting material 50 is used, and the potting material 50 becomes the partitions 8 and 9.

In order to perform the fixing, first, polyurethane liquid for forming the potting material 50 is supplied to both the end portions of the secondary base material 3" inside the cylindrical housing main body 21A. Subsequently, the cylindrical housing main body 21A is placed into a centrifugal separator in its entirety. Thereafter, the polyurethane liquid is cured while being centrifugally maintained at the desired ends. Accordingly, both the end portions of the secondary base material 3" are in a fixed state by the potting material 50 (see FIG. 10(*a*)). Note that, both the end portions of the secondary base material 3" also include the turning-back point 312, the starting point 311, and the ending point 313 which are fixed by using the fixing string 11 in the first step.

As illustrated in FIG. 10, the fifth step is a cutting step in which both the end portions of the secondary base material 3" fixed by using the potting material 50 are individually cut. Accordingly, the hollow fiber membrane layer 3A and the hollow fiber membrane layer 3B can be collectively obtained, wherein many individual open-ended tubes extending between opposite ends of layers 3A and 3B are formed.

In the fifth step, a cutting apparatus 80 illustrated in FIG. 10 is used. The cutting apparatus 80 has two cutters (cutting tools) 801. When each of the cutters 801 approaches the secondary base material 3", both the end portions of the secondary base material 3" are cut. Note that, the cutting apparatus 80 is not limited to the configuration having the cutters 801. However, for example, the cutting apparatus 80 may be configured to spouts water jet or may be configured to perform irradiation with a laser beam.

As illustrated in FIG. 10(*a*), in portions of the secondary base material 3" fixed by using the potting material 50, a first cutting line 351 is set at a portion on the right side from the fixing string 11 in the left end portion, and a second cutting line 352 is set at a portion on the left side from the fixing string 11 in the right end portion as well.

The secondary base material 3" is cut along the first cutting line 351 and the second cutting line 352 by using the cutters 801 of the cutting apparatus 80. Accordingly, as illustrated in FIG. 10(*b*), the secondary base material 3" are divided into three members. The member positioned at the center becomes the hollow fiber membrane layer 3A and the hollow fiber membrane layer 3B. Note that, the members at both ends are discarded.

In addition, as a result of the cutting, in the hollow fiber membrane layer 3B (also similar in the hollow fiber membrane layer 3A), the turning-back point 312 is also removed. Accordingly, both ends of each of the hollow fiber membranes 31 configured to be the hollow fiber membrane layer 3B can be individually open, and the heat medium H can pass through the inside of the hollow fiber membrane 31. Note that, in the hollow fiber membrane layer 3A, the gas G can pass through the inside of each of the hollow fiber membranes 31.

The sixth step is a mounting step in which the first cap 22A and the second cap 23A are individually mounted in the cylindrical housing main body 21A. The oxygenator 10 can be obtained through the mounting. Note that, after being mounted, the first cap 22A and the second cap 23A may be individually fixed to the cylindrical housing main body 21A by using an adhesive or the like, for example.

Second Embodiment

Figure 12:
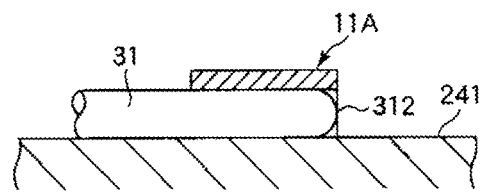
FIG. 12 is a view illustrating a fixed state of the hollow fiber membrane in the base material obtained through the method of manufacturing a heat exchanger of the present invention in a second embodiment.

FIG. 12 is a view illustrating a fixed state of the hollow fiber membrane in the base material obtained through the method of manufacturing a heat exchanger of the present invention (second embodiment).

Hereinafter, with reference to the drawing, the second embodiment of the method of manufacturing a heat exchanger and the heat exchanger according to the present invention will be described. The points different from those in the above-described embodiment will be mainly described, and description of similar contents will be omitted.

The present embodiment is similar to the first embodiment except that the fixing method with respect to the hollow fiber membrane is different.

As illustrated in FIG. 12, in the present embodiment, a flexible fixing belt (belt-like body) 11A is used for fixing the turning-back point 312 of the hollow fiber membrane 31. The fixing belt 11A has a width wider than that of the fixing string 11. Due to the fixing belt 11A, when the portion in the vicinity of the turning-back point 312 of the hollow fiber membrane 31 is pressed, the contact area with respect to the hollow fiber membrane 31 increases. Accordingly, fixing can be more reliably performed.

The configuration material of the fixing belt 11A is not particularly limited. For example, a resin material such as polyethylene and the like can be used.

Third Embodiment

Figure 13:
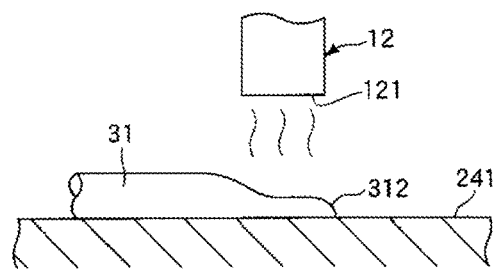
FIG. 13 is a view illustrating a fixed state of the hollow fiber membrane in the base material obtained through the method of manufacturing a heat exchanger of the present invention in a third embodiment.

FIG. 13 is a view illustrating a fixed state of the hollow fiber membrane in the base material obtained through the method of manufacturing a heat exchanger of the present invention in a third embodiment.

Hereinafter, with reference to the drawing, the third embodiment of the method of manufacturing a heat exchanger and the heat exchanger according to the present invention will be described. The points different from those in the above-described embodiments will be mainly described, and description of similar contents will be omitted.

The present embodiment is similar to the first embodiment except that the fixing method with respect to the hollow fiber membrane is different.

As illustrated in FIG. 13, in the present embodiment, the portion in the vicinity of the turning-back point 312 of the hollow fiber membrane 31 is fixed as follows.

First, a dryer 12 is prepared. An exhaust port 121 of the dryer 12 is oriented toward the portion in the vicinity of the turning-back point 312, thereby blowing hot blast from the exhaust port 121. Accordingly, the portion in the vicinity of the turning-back point 312 is heated and softened, and a contact area with respect to the first cylinder member 241 increases. Therefore, friction force between the portion in the vicinity of the turning-back point 312 and the first cylinder member 241 also increases, thereby performing fixing of the hollow fiber membrane 31.

In this manner, in the present embodiment, a separately installed member for fixing the hollow fiber membrane 31 to the oxygenator 10 is omitted. Accordingly, the configuration of the oxygenator 10 is simplified, and it is possible to realize miniaturization of the oxygenator 10. Note that, the hollow fiber membrane 31 may be fixed by using the fixing string 11.

Fourth Embodiment

Figure 14:
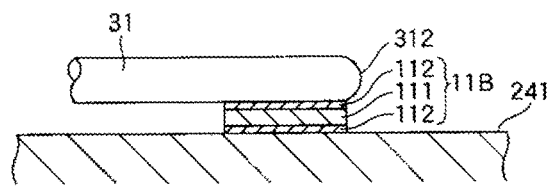
FIG. 14 is a view illustrating a fixed state of the hollow fiber membrane in the base material obtained through the method of manufacturing a heat exchanger of the present invention in a fourth embodiment.

FIG. 14 is a view illustrating a fixed state of the hollow fiber membrane in the base material obtained through the method of manufacturing a heat exchanger of the present invention in a fourth embodiment.

Hereinafter, with reference to the drawing, the fourth embodiment of the method of manufacturing a heat exchanger and the heat exchanger according to the present invention will be described. The points different from those in the above-described embodiments will be mainly described, and description of similar contents will be omitted.

The present embodiment is similar to the first embodiment except that the fixing method with respect to the hollow fiber membrane is different.

As illustrated in FIG. 14, in the present embodiment, a double-sided adhesive tape 11B is used for fixing the turning-back point 312 of the hollow fiber membrane 31. The double-sided adhesive tape 11B is configured to include a flexible belt-like substratum 111 and adhesive layers 112 which are respectively formed on both surfaces of the substratum 111.

Note that, as the substratum 111, for example, it is possible to use the same configuration material as that of the fixing belt 11A adopted in the second embodiment. In addition, the adhesive layer 112 can be configured to be a silicone-based adhesive.

Due to the double-sided adhesive tape 11B having such a configuration, the hollow fiber membrane 31 can be reliably fixed.

Fifth Embodiment

Figure 15:
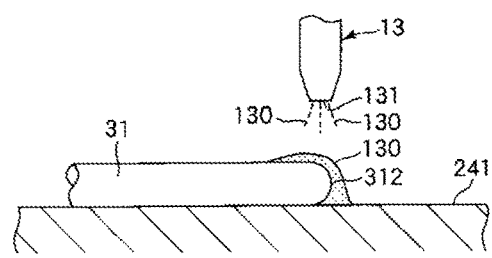
FIG. 15 is a view illustrating a fixed state of the hollow fiber membrane in the base material obtained through the method of manufacturing a heat exchanger of the present invention in a fifth embodiment.

FIG. 15 is a view illustrating a fixed state of the hollow fiber membrane in the base material obtained through the method of manufacturing a heat exchanger of the present invention in a fifth embodiment.

Hereinafter, with reference to the drawing, the fifth embodiment of the method of manufacturing a heat exchanger and the heat exchanger according to the present invention will be described. The points different from those in the above-described embodiments will be mainly described, and description of similar contents will be omitted.

The present embodiment is similar to the first embodiment except that the fixing method with respect to the hollow fiber membrane is different.

As illustrated in FIG. 15, in the present embodiment, the portion in the vicinity of the turning-back point 312 of the hollow fiber membrane 31 is fixed as follows.

First, an apparatus provided with a nozzle 13 having an ejection port 131 which ejects an adhesive 130 is prepared. The ejection port 131 is oriented toward the portion in the vicinity of the turning-back point 312, and coating is performed with the adhesive 130 from the ejection port 131. Accordingly, the adhesive 130 is applied to the portion in the vicinity of the turning-back point 312.

Thereafter, the applied adhesive 130 is forcibly dried or naturally dried, thereby fixing the hollow fiber membrane 31.

Hereinabove, the embodiments illustrating the method of manufacturing a heat exchanger and the heat exchanger of the present invention have been described. However, the present invention is not limited thereto, and an arbitrary step may be added to the method of manufacturing a heat exchanger. In addition, each configuration portion of the heat exchanger may be replaced with an arbitrary configuration portion which can exhibit a similar function. In addition, an arbitrary configuration subject may be added.

In addition, in the method of manufacturing a heat exchanger and the heat exchanger according to the present invention, two or more arbitrary configurations (features) in each of the above-described embodiments may be combined together.

In addition, in the above-described embodiments, each of the hollow fiber membranes configured to be the hollow fiber membrane layer of the oxygenator section and each of the hollow fiber membranes configured to be the hollow fiber membrane layer of the heat exchange section are the same as each other. However, without being limited thereto, for example, the hollow fiber membrane on one side (former membrane) may be thinner than the hollow fiber membrane on the other side (latter membrane), or both the hollow fiber membranes may be configured to be materials different from each other.

In addition, in the above-described embodiments, regarding the oxygenator section and the heat exchange section, the heat exchange section is disposed on the inner side, and the oxygenator section is disposed on the outer side. However, without being limited thereto, the oxygenator section may be disposed on the inner side, and the heat exchange section may be disposed on the outer side. In this case, blood flows down from the outer side toward the inner side.

In addition, when the turned-back portion of the hollow fiber membrane is fixed, the fixing methods described from the first embodiment to the fifth embodiment may be combined together.

Hereinafter, a specific example of the present invention will be described. Note that, the present invention is not limited thereto.

Example 1

A heat exchanger for an artificial heart-lung oxygenator as illustrated in FIGS. 1 to 5 was manufactured. In the heat exchanger for an artificial heart-lung, a housing was configured to be made from polycarbonate. The inner dimensions of the housing were φ90×80 mm.

The hollow fiber membrane was made from polyethylene. The outer diameter $\phi d_2$ of the hollow fiber membrane was 0.5 mm. In addition, the winding state of the hollow fiber membrane, the inclination angle θ, and the length of the hollow fiber membrane per one round trip are indicated in Table 1.

Example 2

Except that the winding state of the hollow fiber membrane, the inclination angle θ, and the length of the hollow fiber membrane per one round trip are set as indicated in Table 1, the heat exchanger for an artificial heart-lung of Example 2 was obtained in a manner similar to that of Example 1.

Example 3

Except that the winding state of the hollow fiber membrane, the inclination angle θ, and the length of the hollow fiber membrane per one round trip are set as indicated in Table 1, the heat exchanger for an artificial heart-lung of Example 3 was obtained in a manner similar to that of Example 1.

Comparative Example 1

Except that the winding state of the hollow fiber membrane is set as indicated in Table 1, similar to that of Example 1, manufacturing of the heat exchanger for an artificial heart-lung of Comparative Example 1 was attempted. However, the hollow fiber membrane was required to be more firmly fixed and the hollow fiber membrane was not wound. Accordingly, the heat exchanger for an artificial heart-lung of Comparative Example 1 could not be manufactured.

Note that, in a case of realizing Comparative Example 1, in order to facilitate winding of the hollow fiber membrane, it is necessary to weave the hollow fiber membrane with the warp or the like in advance. The presence of the warp leads to the concern of adhering of thrombus or the like.

Comparative Example 2

Except that the winding state of the hollow fiber membrane, the inclination angle θ, and the length of the hollow fiber membrane per one round trip are set as indicated in Table 1, the heat exchanger for an artificial heart-lung of Comparative Example 2 was obtained in a manner similar to that of Example 1.

Each of the heat exchangers for an artificial heart-lung of Examples 1 to 3 and Comparative Example 2 was installed in an extracorporeal blood circulation circuit similar to an actual extracorporeal blood circulation circuit, and a simulation of gas exchange and heat exchange was performed.

In the simulated usage state, regarding the heat exchangers for an artificial heart-lung of Examples 1 to 3 and Comparative Example 2, the heat exchanger effectiveness based on the requirement in JIS T 1704, the filling amount (maximum) of blood filling the heat exchanger for an artificial heart-lung, and the pressure loss (maximum) of the heat medium (water) in the hollow fiber membrane layer were measured.

Moreover, regarding the heat exchangers for an artificial heart-lung of Examples 1 to 3 and Comparative Example 2, in accordance with Evaluation Standard 1 described below, whether or not each of the heat exchanger for an artificial heart-lung is suitable is actual usage was generally evaluated.

Evaluation Standards shown in Table 1 include rankings of A: highly improved over the existing heat exchanger for an artificial heart-lung, B: improved over the existing heat exchanger for an artificial heart-lung, and C: equal to or poorer than the existing heat exchanger for an artificial heart-lung.

Hereinbefore, preferable embodiments of the present invention have been described. However, the present invention is not limited to the above-described embodiments, and it is needless to mention that various modifications and changes can be made without departing from the gist and the scope of the present invention.

According to the present invention, there is provided a method of manufacturing a heat exchanger including a hollow fiber membrane layer that is configured to include a plurality of hollow fiber membranes each of which has a hollow portion allowing a heat medium to pass therethrough and is obtained from a base material in which the plurality of hollow fiber membranes are accumulated so as to form an overall shape of a cylindrical body. The method includes a winding step of winding each of the hollow fiber membranes about an axis of the cylindrical body while the hollow fiber membrane is caused to be wound along an axial direction of the cylindrical body so as to obtain the base material. In the winding step, each of the hollow fiber membranes is wound about the axis of the cylindrical body within a range from one round to less than two rounds during one round trip in which the hollow fiber membrane starts from one side toward the other side of the cylindrical body in the axial direction, turns back at the other side, and returns to the one side again. Therefore, excellent heat exchanger effectiveness can be obtained, and a filling amount of a fluid can be reduced when the fluid which becomes a target subjected to heat exchange thereof passes through between hollow fiber membranes.

What is claimed is:

1. A method of manufacturing a heat exchanger having a hollow fiber membrane layer and comprised of a plurality of hollow fiber membrane conduits each of which has a hollow portion allowing a heat medium to pass therethrough, the method comprising the steps of:

TABLE 1

| | Comparative Example | Example 1 | Example 2 | Example 3 | Comparative Example 2 |
|---|---|---|---|---|---|
| Winding state of hollow fiber membrane | 0.45 windings | 0.60 windings | 0.75 windings | 0.80 windings | 1 winding |
| Inclination angle (traverse angle) θ [°] | — | 50.6 to 54.6 | 56.7 to 60.7 | 58.4 to 62.4 | 63.8 to 67.8 |
| Length of hollow fiber membrane per one round trip [mm] | — | 128 | 150 | 158 | 187 |
| Heat exchanger effectiveness [/m$^2$] | — | 0.91 | 0.99 | 0.81 | 1.00 |
| Blood filling amount [mL/m$^2$] | — | 50.0 | 43.4 | 44.6 | 41 |
| Pressure loss of heat medium [mmHg/m$^2$] | — | 308.1 | 321.6 | 337.9 | 491 |
| Evaluation | failed to be manufactured (C) | B | A | B | C |

As is evident from Table 1, the result shows that the heat exchanger for an artificial heart-lung of Example 2 among those of Examples 1 to 3 is highly suitable for actual usage and the heat exchangers for an artificial heart-lung of Examples 1 and 3 are suitable for actual usage next thereto.

In addition, when the heat exchangers for an artificial heart-lung respectively including the hollow fiber membrane layers of FIGS. 11 to 15 are manufactured and an evaluation similar to the previous evaluation is performed, substantially the same result as that of each of Examples is obtained.

providing a cylindrical body for supporting the fiber membrane layer, wherein the cylindrical body has an outer surface defining a longitudinal axis and first and second longitudinal ends;

winding a continuous base cord of hollow fiber membrane onto the cylindrical body along a generally helical trajectory around the longitudinal axis with a plurality of continuous round trips from the first end to the second end and turning back at each respective end, wherein each round trip completes a number of circumferential revolutions N, wherein N is greater than or equal to one, wherein N is less than two, wherein an inclination angle of the hollow fiber membrane between turning-back portions ranges from 40° to 70°, and wherein each turning-back portion is folded at an acute angle;

continuously fixing in place each respective turning-back portion at the first end and the second end during the winding of the base cord;

cutting longitudinal end portions from the fiber membrane layer, thereby removing the turning-back portions to introduce open ends for the hollow fiber membrane conduits;

wherein the winding step satisfies an expression Traverse [mm/rotation]×N=traverse oscillation width×2±(outer diameter of hollow fiber membrane+gap between hollow fiber membranes adjacent to each other)×total number of hollow fiber membranes (where N satisfies 1≤N<2).

2. The method of claim 1 wherein N satisfies 1.2≤N≤1.6.

3. The method of claim 1 wherein the step of fixing in place each respective turning-back portion is comprised of continuously winding a respective flexible fixing body at the first and second ends to compress each respective turning-back portion;

wherein the cutting step removes the fixing bodies.

4. The method of claim 3 wherein the fixing bodies are each comprised of a flexible string-like body.

5. The method of claim 3 wherein the fixing bodies are each comprised of a flexible belt-like body.

6. The method of claim 1 wherein the step of fixing in place each respective turning-back portion is comprised of subjecting the turning-back portion to heat-melting.

7. The method of claim 1 wherein the step of fixing in place each respective turning-back portion is comprised of applying an adhesive.

8. The method of claim 1 wherein the base cord of hollow fiber membrane is comprised of a polyolefin-based resin.

9. The method of claim 1 wherein an outer diameter of the base cord of hollow fiber membrane is equal to or less than 1 mm.

* * * * *